United States Patent [19]

Jiskoot

[11] 4,307,620
[45] Dec. 29, 1981

[54] LIQUID SAMPLING SYSTEM

[76] Inventor: Joost J. Jiskoot, 85 Goods Station Rd., Tunbridge Wells, Kent, England

[21] Appl. No.: 72,290

[22] Filed: Sep. 4, 1979

[30] Foreign Application Priority Data

Mar. 4, 1978 [GB] United Kingdom ............... 35540/78

[51] Int. Cl.³ .............................................. G01N 1/14
[52] U.S. Cl. ................................. 73/863.83; 73/863.61
[58] Field of Search ........... 73/422 R, 863.41, 863.43, 73/863.53, 863.61, 863.83, 863.86

[56] References Cited

U.S. PATENT DOCUMENTS

| | | | |
|---|---|---|---|
| 2,322,018 | 6/1943 | Huber | 73/422 R |
| 2,363,625 | 11/1944 | Swearingen | 73/422 R |
| 2,807,961 | 10/1957 | Grimes | 73/422 R |
| 3,282,113 | 11/1966 | Sachnik | 73/422 R |
| 3,985,624 | 10/1976 | Prevost et al. | 73/422 R |

Primary Examiner—Daniel M. Yasich

[57] ABSTRACT

Liquid is removed from a liquid transfer line 1, for example a crude oil pipeline, through a sampling probe 2 and returned to the transfer line 1 via a return loop 3 and pump 5. At the outlet 4 of the return loop to the transfer line the returning liquid enters the liquid in the transfer line as a jet or jets which agitates the liquid to a substantially homogeneous mixture. The outlet 4 is upstream of probe 2 so that in operation the liquid entering the return loop 3 is uniformly mixed and a representative sample may be withdrawn from the return loop 3 into sample outlet through valves 9 and 10. To ensure mixing of sedimentary layers in the transfer line 1 the jet from outlet 4 is directed upwardly into the transfer line.

7 Claims, 1 Drawing Figure

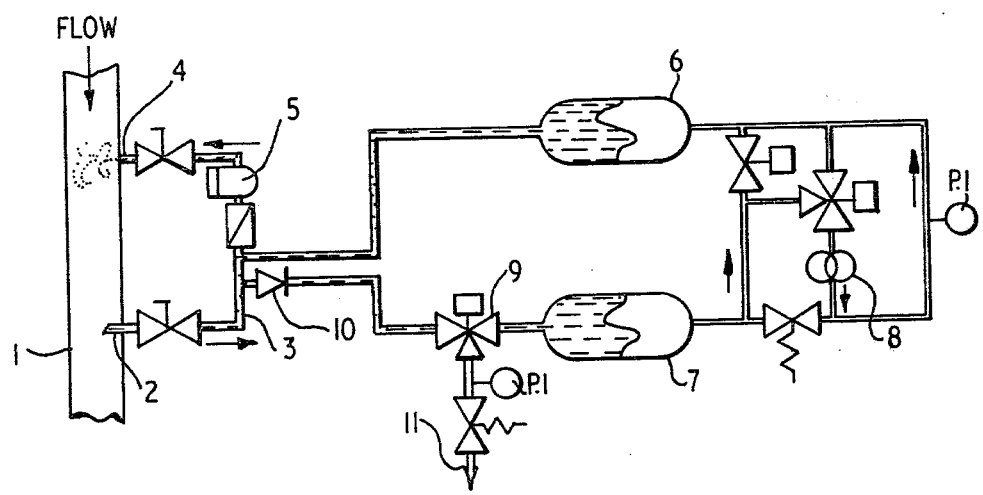

LIQUID SAMPLING SYSTEM

This invention is concerned with a liquid sampling system, particularly for taking samples from crude oil pipelines.

The automatic collection of representative samples during liquid transfer operations has become increasingly important in recent years, both for batching operations, such as tanker unloading, and for pipeline operations, where the flow rate is variable but continuous. The collected samples, which are used for laboratory analysis or retained for reference, are particularly important to determine crude oil properties for fiscal purposes. It is therefore important that the sample should be taken from a homogeneous liquid flow, but this is difficult with conventional sampling systems in which a sampling probe is inserted into the transfer line, because of layering of the liquid in the transfer line, which is particularly a feature of a crude oil pipeline flow. Static or mechanically driven mixers in the transfer line upstream of a sampling probe would be unsatisfactory, since static mixers can only be serviced during shut down and would not allow pigging, and mechanical mixers would have to be very substantially constructed to withstand the flow velocities, and so would be difficult to insert and withdraw.

According to one aspect of the present invention there is provided a method of obtaining a homogeneous sample from a liquid transfer line comprising removing liquid from the liquid transfer line and returning it to the transfer line through a return loop so that it re-enters the transfer line as a jet or jets of liquid which agitate the liquid in the transfer line to a substantially uniform mixture, and removing a sample from the uniform mixture.

The sample may be removed from the return loop, in which case the outlet of the return loop to the transfer line is upstream of the inlet to the return loop and the distance between the inlet and outlet and the flow velocity in the return loop are selected empirically to ensure that the liquid in the transfer line is uniformly mixed at the inlet to the return loop.

The volume of the return loop and the upstream position of the mixing jet(s) provide an integrating feature which evens out longitudinal quality variations of the liquid in the transfer line. Alternatively the sample may be obtained conventionally directly from the transfer line down stream of the outlet of the return loop at any point at which the liquid remains a uniform mixture.

A pump will normally be provided in the return loop to achieve a flow velocity in the return loop which gives satisfactory agitation of the liquid in the transfer line. The pump may be of variable rate so as to achieve isokinetic sampling, if this is desired.

According to another aspect of the invention there is provided an installation for sampling liquid in a liquid transfer line comprising a return loop including a pump to remove liquid from the transfer line and return it to the transfer line upstream of the point of removal as a jet or jets which agitate the liquid in the transfer line to a substantially homogeneous mixture, and means for taking a sample of liquid from the return loop.

According to a further aspect of the invention there is provided an installation for sampling liquid in a liquid transfer line comprising a return loop including a pump to remove liquid from the transfer line and return it to the transfer line as a jet or jets which agitate the liquid in the transfer line to a substantially homogeneous mixture, and means for taking a sample of liquid from the transfer line downstream of the outlet of the return loop.

In a crude oil pipe line, layers of water and sediment-containing crude oil tend to flow at the bottom of the pipeline. To ensure satisfactory mixing of these layers the outlet of the return loop is preferably directed upwards into the transfer line and is flush with the internal surface of the transfer line. The latter also is desirable to allow pigging, although a retractable nozzle could be used if desired. Under normal sampling practice, the inlet to a sampler is a probe inserted $\frac{1}{3}$–$\frac{1}{2}$ diameter into the transfer line, and also this probe is preferably retractable. However, as a result of the mixing provided by the return loop, such a probe is really no longer necessary, and sample inlet and the return loop inlet (which acts as the sample inlet when the sample is removed from the return loop) can also be flush with the internal surface of the transfer line.

The sample of liquid taken from the return loop or the transfer line may be obtained by any conventional sampling system. For accurate sampling there is preferably used a precision rotary metering pump which is pressure balanced so that line pressure is maintained on both sides of the metering pump. The sampling system is normally associated with a flow meter in the transfer line to obtain a flow responsive mode of sampling. Alternatively a time proportional control may be used where the flow rate in the transfer line is practically constant.

The samples removed from the return loop or transfer line are fed to a sample receiver for subsequent analysis. With crude oil this may be a pressurized sample receiver or a split phase sample collection system which separates the gaseous component and stores them in gas sample collectors separate from the liquid components.

The accompanying drawing indicates diagrammatically a sampling system in accordance with the present invention.

Referring to the drawing, crude oil passing through a pipeline 1 is intercepted by a retractable sampling probe 2 which forms the inlet for a return loop 3. Oil entering the return loop 3 is returned to the pipeline 1 through one or more mixing jets 4. The flow velocity in the return loop 3 is controlled by a pump 5 and, by suitable adjustment of the flow velocity and selection of the numbers and diameter of the mixing jets 4, the stream of oil re-entering the pipeline through the jets 4 from the return loop 3 agitates the crude oil in the pipeline 1 sufficiently to ensure that it is a homogeneous mixture when it reaches the probe 2 which is the inlet to the return loop 3.

Samples of the oil in the return loop 3 may be removed by conventional sampling procedure. The system shown in the drawing is a pressure balanced system in which a hydraulic equaliser (pressure balancing vessel) 6 and sample collector 7 are both connected to the return loop 3 so that line pressure is maintained on both sides of a sample metering pump 8. The metering pump 8 operates at a known flow rate so that when a sampling valve 9 is opened for a known length of time an accurate volume of hydraulic oil can be transferred from the sample collector 7 and discharged into the hydraulic equaliser 6, causing an equal volume of the crude oil sample to be injected into the sample collector via a non-return valve 10. By reversing the flow of hydraulic oil from the hydraulic equaliser 6 to the sample collector 7 and altering the flow path through the valve 9, the sample is discharged through sample outlet 11 into a sample receiver (not shown). P.I on the drawing indicates a pressure indicator or pressure gauge.

I claim:

1. A method of obtaining a homogeneous sample from a liquid transfer line in the form of a closed pipe comprising removing liquid from the transfer line and returning it to the transfer line through a return loop including a pump so that it enters the transfer line under the action of the pump as at least one jet of liquid transverse to the direction of flow through the transfer line to agitate the liquid in the transfer line to a substantially uniform mixture, and removing a sample from the uniform mixture.

2. A method according to claim 1 in which the outlet of the return loop to the transfer line is upstream of the inlet to the return loop and the sample is removed from the liquid in the return loop.

3. A method according to claim 1 in which the sample is removed from the liquid in the transfer line downstream of the outlet of the return loop to the transfer line.

4. A method according to claim 1 in which the at least one jet of liquid are introduced upwardly into the transfer line.

5. An installation for sampling liquid in a liquid transfer line in the form of a closed pipe comprising a return loop including a pump, an inlet means for the return loop to remove liquid from the transfer line and a jet means at an outlet of the return loop to return the liquid to the transfer line upstream of the inlet means, the pump and the jet means being adapted to return the liquid from the return loop to the transfer line as at least one jet transversely to the direction of flow through the transfer line to agitate the liquid in the transfer line to a substantially homogeneous mixture, and means for taking a sample of liquid from the return loop.

6. An installation for sampling liquid in a liquid transfer line in the form of a closed pipe comprising a return loop including a pump, an inlet means for said return loop extending into said closed pipe to remove liquid from the transfer line and a jet means in the closed pipe to return the liquid from the return loop to the transfer line under the action of the pump as at least one jet transversely to the direction of flow through the transfer line to agitate the liquid in the transfer line to a substantially homogenous mixture, and means for taking a sample of liquid from the transfer line downstream of the jet means of the return loop.

7. An installation according to claim 5 in which the jet means of the return loop to the transfer line is at the bottom of the transfer line and directed upwardly into the transfer line.

* * * * *